(12) United States Patent
Maniar

(10) Patent No.: US 9,060,967 B2
(45) Date of Patent: Jun. 23, 2015

(54) STABLE AQUEOUS FORMULATION OF (E)-4-CARBOXYSTYRYL-4-CHLOROBENZYL SULFONE

(75) Inventor: Manoj Maniar, Fremont, CA (US)

(73) Assignee: ONCONOVA THERAPEUTICS, INC, Newtown, NJ (US)

(*) Notice: Subject to any disclaimer, the term of this patent is extended or adjusted under 35 U.S.C. 154(b) by 0 days.

(21) Appl. No.: 13/636,310

(22) PCT Filed: Mar. 24, 2011

(86) PCT No.: PCT/US2011/029840
§ 371 (c)(1),
(2), (4) Date: Sep. 20, 2012

(87) PCT Pub. No.: WO2011/119863
PCT Pub. Date: Sep. 29, 2011

(65) Prior Publication Data
US 2013/0012589 A1    Jan. 10, 2013

Related U.S. Application Data

(60) Provisional application No. 61/318,100, filed on Mar. 26, 2010.

(51) Int. Cl.
| | | |
|---|---|---|
| A61K 31/10 | (2006.01) |
| A61K 9/107 | (2006.01) |
| A61K 31/192 | (2006.01) |
| A61K 47/22 | (2006.01) |
| A61K 47/34 | (2006.01) |
| A61P 39/02 | (2006.01) |
| A61K 9/08 | (2006.01) |

(52) U.S. Cl.
CPC . *A61K 31/10* (2013.01); *A61K 9/08* (2013.01); *A61K 47/34* (2013.01); *A61K 31/192* (2013.01); *A61K 9/1075* (2013.01); *A61K 47/22* (2013.01)

(58) Field of Classification Search
CPC ..... A61K 31/10; A61K 31/192; A61K 47/22; A61K 47/34; A61K 9/1075
USPC ............................. 514/568, 710, 709; 568/34
See application file for complete search history.

(56) References Cited

U.S. PATENT DOCUMENTS

| | | | |
|---|---|---|---|
| 6,656,973 B2 | 12/2003 | Cosenza et al. | |
| 6,667,346 B2 | 12/2003 | Reddy et al. | |
| 6,982,282 B2 | 1/2006 | Lambert et al. | |
| 8,063,109 B2 * | 11/2011 | Bell et al. | 514/710 |
| 2009/0247624 A1 * | 10/2009 | Bell et al. | 514/461 |

FOREIGN PATENT DOCUMENTS

| | | |
|---|---|---|
| WO | PCT/US05/025224 | 1/2006 |
| WO | PCT/US06/029109 | 2/2007 |
| WO | PCT/US08/00523 | 7/2008 |
| WO | PCT/US07/016879 | 9/2008 |

OTHER PUBLICATIONS

Dash S K et al.: "Preformulation development of a parenteral formulation for ON 01210.Na, a radioprotectant" AAPS Annual Meeting and Exposition,(Online] Nov. 5, 2005.
Alfieri A A et al: "Radiation damage protection by the benzylstyrl sulfone analog, Ex-Rad" International Journal of Radiation Oncology Biology Physics, vol. 60, No. 1(2004).
Strickley et al: "Solubilizing Exipients in Oral and Injectable Formulations" Pharmaceutical Research, Kluwe Academic Publishers, New York, NY, US vol. 21, No. 2, (2004).
ISR, Jun. 21, 2011, Onconova Therapeutics Inc.

* cited by examiner

*Primary Examiner* — Sreeni Padmanabhan
*Assistant Examiner* — Irina Neagu
(74) *Attorney, Agent, or Firm* — Houri Khalilian; Serge Sira; Law Offices of Khalilian Sira, LLC

(57) ABSTRACT

An aqueous pharmaceutical solution composition comprising between about 20 mg/ml to about 100 mg/ml of a radioprotective α,β-unsaturated aryl sulfone, a cosolvent comprising polyethylene glycol (PEG), polypropylene glycol, polyglycerol, DMA, propylene glycol, glycerol, ethanol, sorbitol, isopropyl alcohol, or a combination thereof in an amount between about 25% and about 90% w/v, and a water soluble Vitamin E derivative, wherein the composition has a pH within the range of about 7.0 to about 9.5.

14 Claims, 6 Drawing Sheets

(E)-4-Carboxystyryl-4-Chlorobenzyl sulfone

ON 01210.Na

Formulation A (ON 1210 Na without Vitamin E TPGS), Time 0, 25 °C / 60% RH

Formulation A (ON 1210 Na without Vitamin E TPGS), Time 3 Months, 25 °C / 60% RH Formulation B (ON 1210 Na with Vitamin E TPGS), Time 0, 25 °C / 60% RH Formulation B (ON 1210 Na with Vitamin E TPGS), Time 3 Months, 25 °C / 60% RH Formulation B (ON 1210 Na with Vitamin E TPGS), Time 3 Months, 40 °C / 75% RH

US 9,060,967 B2

STABLE AQUEOUS FORMULATION OF (E)-4-CARBOXYSTYRYL-4-CHLOROBENZYL SULFONE

This application derives priority from U.S. Provisional Application No. 61/318,100, filed Mar. 26, 2010, and the PCT Patent Application No. PCT/US2011/029840, filed on Mar. 24, 2011, the entire contents of which is incorporated herein by reference.

FIELD OF THE INVENTION

The invention relates to stable solution formulations for effective pharmacological delivery of the cytoprotective agent α,β-unsaturated aryl sulfone.

BACKGROUND OF THE INVENTION

While anti-radiation suits or other protective gear may be effective at reducing radiation exposure, such gear is expensive, unwieldy, and generally not available to public. Moreover, radioprotective gear will not protect normal tissue adjacent to a tumor from stray radiation exposure during radiotherapy. Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., Semin. Radiat. Oncol. 6:306-320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Maisin, J. R., Bacq and Alexander Award Lecture. "Chemical radioprotection: past, present, and future prospects", Int J. Radiat Biol. 73:443-50, 1998). Pharmaceutical radiation sensitizers, which are known to preferentially enhance the effects of radiation in cancerous tissues, are clearly unsuited for the general systemic protection of normal tissues from exposure to ionizing radiation.

The major biological effects of radiation exposure are the destruction of bone marrow cells, gastrointestinal (GI) damage, lung pneumonitis, and central nervous system (CNS) damage. The long-term effects of radiation exposure include an increase in cancer rates. It has been estimated that the exposure of 100 rems (roentgen equivalent man: a measurement used to quantify the amount of radiation that would produce harmful biological effects) would produce ARS symptoms. Exposure levels above 300 rems would result in the death of approximately 50% of the exposed population.

The α,β-unsaturated aryl sulfones, in particular benzyl styryl sulfones, provide significant and selective systemic protection of normal cells from radiation-induced damage in animals. When used in radiotherapy techniques, these compounds also exhibit independent toxicity to cancer cells. These α,β-unsaturated aryl sulfones, in particular benzyl styryl sulfones, are described in U.S. Pat. Nos. 6,656,973 and 6,667,346, which are particularly incorporated herein by reference in their entirety. Although these compounds are stable in solid state their aqueous formulations for parenteral administration are pH sensitive and pose challenging hurdles to overcome physical stability. The most likely causative factor may be attributed to the reactive styryl sulfone conjugated double bond, which is prone to Michael addition by nucleophiles and eventual fallout of the conjugated addition product.

U.S. Pat. No. 6,656,973, describes in vitro pharmacological effects of DMSO solubilization of a benzyl styryl sulfone (e.g. ON 01210.NA) but fails to disclose a composition comprising ON 01210.NA formulation and specifically, a shelf stable formulation which is suitable for administration to humans.

PCT Application WO 2007/016201 describes pharmaceutical solution compositions for parenteral administration for reducing toxic effects of ionizing radiation in a subject, comprising an effective amount of at least one radioprotective α,β-Unsaturated aryl sulfone, and at least one component selected from the group consisting of a) a water soluble polymer in an amount between about 0.5% and about 90% w/v, b) at least one chemically modified cyclodextrin in an amount between about 20% and about 60% w/v, and c) DMA in an amount between 10% and about 50% w/v.

U.S. Patent Application 20090247624, and corresponding PCT Application WO 2008/105808, are directed to aqueous solutions, which comprise between about 20 mg/ml to about 100 mg/ml of at least one α,β-unsaturated aryl sulfone (e.g., the compound ON 01210.Na ((E)-4-Carboxystyryl-4-chlorobenzylsulfone sodium salt, a cosolvent in an amount between about 25% and about 90% w/v (e.g., about 50% PEG 400), wherein the composition is buffered and exists within the range of about pH 7.0 to about pH10 (e.g., 0.2M Tris-EDTA, pH about 8.5).

The aforementioned solution formulations have exhibited a sub-optimal shelf life and lack a preferred degree of solubility and/or stability. These formulations evolved progressively as a result of addressing the most challenging aspects in the formulation and drug development field, namely, solubility and stability parameters that defined the long term viability of these formulations. There seems to be a delicate balance between pH, solubility and stability of the active moiety in aqueous milieu, wherein achieving such balance and development of a shelf stable aqueous formulation has presented a formidable challenge. Therefore, a shelf stable effective solution formulation that prevents the breakdown of the therapeutically active entity and keeps the drug in the solution at the desired pH was most desired and significant effort was directed towards this goal.

What is needed therefore, is a shelf stable effective solution formulation of radioprotective α,β-unsaturated aryl sulfones that prevents the breakdown of the therapeutically active entity and keeps the drug in the solution at the desired pH. This invention solves these and other long felt needs by providing improved solution formulation of radioprotective α,β-unsaturated aryl sulfones having improved physical and chemical stability and enhanced shelf life.

SUMMARY OF THE INVENTION

In one embodiment, the disclosure of this invention specifically removes and provisos out any prior formulations of αβ unsaturated aryl sulfones that were formulated in the absence of a water soluble Vitamin E derivatives including, by way of example and not limitation, Vitamin E TPGS (d-alpha tocopheryl polyethylene glycol 1000 succinate), Tocopheryl succinate, 6-Hydroxy-2,5,7,8-tetramethylchroman-2-carboxylic Acid (Trolox), and tocopherol monoglucoside (TMG).

In one aspect, the invention discloses an aqueous pharmaceutical solution composition comprising between about 20 mg/ml to about 100 mg/ml of at least one radioprotective α,β-unsaturated aryl sulfone and at least one cosolvent comprising a water soluble polymer including, by way of example and not limitation, polyethylene glycol (PEG), polypropylene glycol, polyglycerol, DMA, propylene glycol, glycerol, ethanol, sorbitol, isopropyl alcohol or a combination thereof in an amount between about 25% and about 90% w/v, and at least one stabilizing agent comprising a water soluble Vitamin E derivative including, by way of example and not limitation, Vitamin E TPGS, Tocopheryl succinate, 6-Hydroxy-2,5,7,8-tetramethylchroman-2-carboxylic Acid (Trolox), tocopherol monoglucoside (TMG), or a combination thereof wherein the composition has a pH within the range of about 7.0 to about 9.5.

In one embodiment, the stabilizing agent is Vitamin E TPGS and the radioprotective compound has the formula:

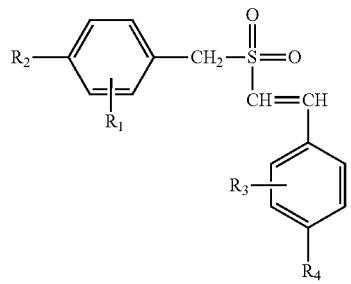

wherein $R_1$ and $R_3$ are hydrogen, $R_2$ is halogen and $R_4$ is carboxy and the steric configuration around the double bond is E.

In another embodiment, the radioprotective compound is (E)-4-carboxystyryl-4-chlorobenzylsulfone.

In yet another embodiment, the radioprotective compound is the sodium salt of (E)-4-carboxystyryl-4-chlorobenzylsulfone (ON 01210.Na).

In one embodiment, the composition comprises between about 20 mg/ml to about 100 mg/ml of the compound (ON 01210.Na); at least one buffer selected from the group consisting of Tris-EDTA, sodium citrate, potassium citrate, sodium phosphate, potassium phosphate, sodium bicarbonate, potassium bicarbonate, lysine-HCl; Arginine-HCl; a cosolvent within the range of about 40% w/v to about 60% w/v; and Vitamin E TPGS is in an amount between about 0.1% and about 10% wherein the composition has a pH within the range of about 8 to about 9.

In another embodiment, Tris-EDTA buffer is composed of Tris within the range of about 0.005M to about 0.5M and EDTA is within the range of about 0.0005M to about 0.05M; PEG is within the range of about 40% w/v to about 60% w/v; and Vitamin E TPGS is in an amount between about 0.1% and about 10% wherein the composition has a pH within the range of about 8.3 to about 8.7

In yet another embodiment, the Tris-EDTA buffer is composed of Tris within the range of about 0.1M to about 0.3M and EDTA within the range of about 0.01M to about 0.03M; PEG 400 is within the range of about 40% w/v to about 60% w/v; and Vitamin E TPGS is in an amount between about 0.25% and about 5% wherein the composition has a pH within the range of about 8.3 to about 8.7

In another embodiment, the composition comprises between about 20 mg/ml to about 60 mg/ml of the compound (ON 01210.Na); Tris-EDTA is composed of Tris within the range of about 0.15M to about 0.25M and EDTA within the range of about 0.015M to about 0.025M; PEG 400 is within the range of about 45% w/v to about 55% w/v; and Vitamin E TPGS in an amount between about 0.5% and about 2.5% wherein the composition has a pH within the range of about 8.4 to about 8.6, and the compound is substantially stable in the composition at about 40° C. for at least about 90 days.

In yet another embodiment, the composition comprises about 25 mg/ml or about 50 mg/ml of the compound (ON 01210.Na); about 0.2M Tris-EDTA buffer composed of Tris of about 0.2M and EDTA of about 0.02M; about 50% w/v PEG 400; and about 1% Vitamin E TPGS wherein the composition has a pH within the range of about 8.4 to about 8.6, and the compound is substantially stable in the composition at about 40° C. for at least about 90 days.

In another aspect, the invention provides a method of preventing, reducing or eliminating the effects of ionizing radiation in a subject who has incurred or is at risk for incurring exposure to ionizing radiation, comprising administering to the subject an effective amount of an aqueous solution composition comprising between about 20 mg/ml to about 100 mg/ml of at least one radioprotective α,β-unsaturated aryl sulfone and at least one cosolvent comprising a water soluble polymer including polyethylene glycol (PEG), polypropylene glycol, polyglycerol, DMA, propylene glycol, glycerol, ethanol, sorbitol, isopropyl alcohol, or a combination thereof, in an amount between about 25% and about 90% w/v, and at least one stabilizing agent consisting of a water soluble Vitamin E derivative including Vitamin E TPGS, Tocopheryl succinate, 6-Hydroxy-2,5,7,8-tetramethylchroman-2-carboxylic Acid (Trolox), tocopherol monoglucoside (TMG), or a combination thereof, wherein the composition has a pH within the range of about 7.0 to about 9.5.

In one embodiment, the solution is administered prior to, concomitant with and/or after the exposure to ionizing radiation.

In another embodiment, the radiation comprises clinical or non-clinical ionizing radiation which can be anticipated, planned or inadvertent. The clinical ionizing radiation includes, by way of example and not limitation, radiation used in clinical settings in diagnostic systems and assay, radiation used for prevention, treatment or amelioration of symptoms of disease or disorder such as cancer (e.g., radiotherapy), among others. The non-clinical ionizing radiation includes, by way of example and not limitation, environmental and atmospheric radiation whether natural or man-made, radiation caused by nuclear weapons, terrorist attack, war, etc.

In yet another aspect, the invention provides a pharmaceutical Kit comprising one or more containers filled with one or more of the ingredients of the pharmaceutical compositions of the invention, mixed together in one or more vials or pre-mixed in separate vials, comprising between about 20 mg/ml to about 100 mg/ml of at least one radioprotective α,β-unsaturated aryl sulfone and at least one cosolvent comprising a water soluble polymer such as, by way of example and not limitation, polyethylene glycol (PEG), polypropylene glycol, polyglycerol, DMA, propylene glycol, glycerol, ethanol, sorbitol, and isopropyl alcohol, in an amount between about 25% and about 90% w/v, and at least one stabilizing agent comprising a water soluble Vitamin E derivative such as, by way of example and not limitation, Vitamin E TPGS, Tocopheryl succinate, 6-Hydroxy-2,5,7,8-tetramethylchroman-2-carboxylic Acid (Trolox), and tocopherol monoglucoside (TMG), wherein the composition has a pH within the range of about 7.0 to about 9.5, a notice in the form prescribed by a governmental agency regulating the manufacture, use or sale of the pharmaceuticals, and an instruction for use of the pharmaceutical for human administration.

In another embodiment, the invention is directed to pharmaceutical compositions for administration for reducing toxic effects of ionizing radiation in a subject, comprising an effective amount of at least one radioprotective α,β-unsaturated aryl sulfone, and at least one component selected from the group consisting of a) a water soluble polymer/cosolvent in an amount between about 0.5% and about 90% w/v, b) and a drug stability enhancing agent in an amount between 0.1 and 10% w/v, wherein the compositions are buffered and exist within the range of about pH 7.0 to about pH10.

Other preferred embodiments of the invention will be apparent to one of ordinary skill in the art in light of what is known in the art, in light of the following drawings and description of the invention, and in light of the claims.

BRIEF DESCRIPTION OF THE FIGURES

FIG. 5 shows the radioprotective effect of ON 01210.Na formulation with TPGS when administered either subcutaneously or orally to mice before the exposure of mice to lethal doses of radiation.

FIG. 6 shows the radiomitigation effect of ON 01210.Na formulation with TPGS when administered either subcutaneously or orally to mice after the exposure of mice to lethal doses of radiation.

DETAILED DESCRIPTION OF THE INVENTION

Figure 1:
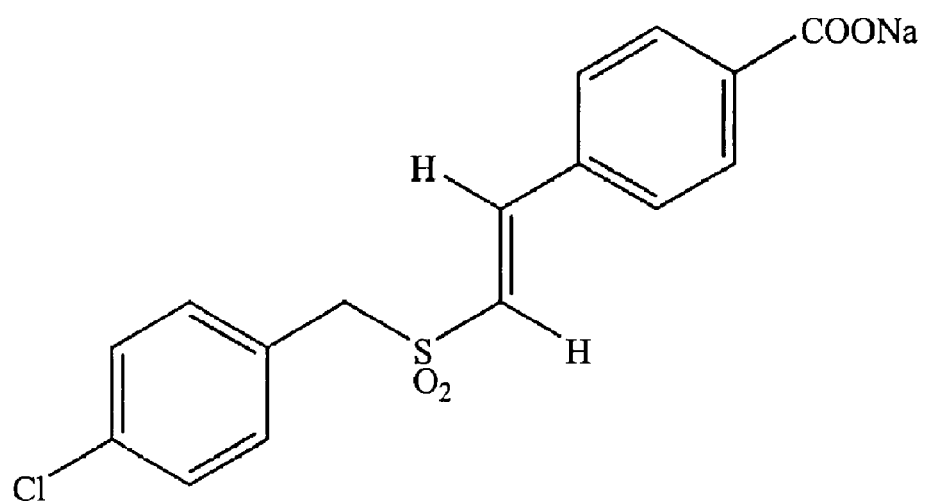
FIG. 1 shows the structure of the sodium salt of 4-chlorobenzyl-4-carboxystyrylsulfone (ON 01210.Na).

Unless defined otherwise, all technical and scientific terms used herein have the same meaning as is commonly understood by one of skill in the art to which this invention belongs. All publications and patents referred to herein are incorporated by reference. The entireties of the disclosures of U.S. Pat. Nos. 6,656,973, 6,667,346, U.S. Patent Application 20090247624 and PCT Applications WO 2007/016201 and WO 2008/105808 are particularly incorporated herein by reference.

DEFINITIONS

As used herein, "about" refers to numerical values that are within the range of 10% above or 10% below the stated numerical value.

As used herein, a numerical range includes all its integer amounts. It is intended herein that by recitation of any specified ranges, the ranges recited also include all those specific integer amounts between the recited range. For example, in the range of about 75% and 100%, includes numerical values of 76% to 99%, 77% to 98%, etc, without actually reciting each specific range therewith.

As used herein, "therapy" is generically used to include all clinical applications including diagnostic, prevention, treatment and amelioration of symptoms of disease and disorder.

As used herein, "α,β unsaturated aryl sulfone" is meant a chemical compound containing one or more α,β unsaturated aryl sulfone groups:

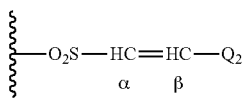

wherein $Q_2$ is substituted or unsubstituted aryl, and the hydrogen atoms attached to the α and β carbons are optionally replaced by other chemical groups.

As used herein, "substituted" means that an atom or group of atoms has replaced hydrogen as the substituent attached to a ring atom. The degree of substitution in a ring system may be mono-, di-, tri- or higher substitution.

As used herein, "aryl" employed alone or in combination with other terms, means, unless otherwise stated, a carbocylic aromatic system containing one or more rings (typically one, two or three rings) wherein such rings may be attached together in a pendent manner or may be fused. Examples include phenyl; anthracyl; and naphthyl, particularly, 1-naphthyl and 2-naphthyl. The aforementioned listing of aryl moieties is intended to be representative, not limiting. It is understood that the term "aryl" is not limited to ring systems with six members.

As used herein, "heteroaryl" by itself or as part of another substituent means, unless otherwise stated, an unsubstituted or substituted, stable, mono- or multicyclic heterocyclic aromatic ring system which consists of carbon atoms and from one to four heteroatoms selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of such heteroaryls include benzimidazolyl, particularly 2-benzimidazolyl; benzofuryl, particularly 3-, 4-, 5-, 6- and 7-benzofuryl; 2-benzothiazolyl and 5-benzothiazolyl; benzothienyl, particularly 3-, 4-, 5-, 6-, and 7-benzothienyl; 4-(2-benzyloxazolyl); furyl, particularly 2- and 3-furyl; isoquinolyl, particularly 1- and 5-isoquinolyl; isoxazolyl, particularly 3-, 4- and 5-isoxazolyl; imidazolyl, particularly 2-, -4 and 5-imidazolyl; indolyl, particularly 3-, 4-, 5-, 6- and 7-indolyl; oxazolyl, particularly 2-, 4- and 5-oxazolyl; purinyl; pyrrolyl, particularly 2-pyrrolyl, 3-pyrrolyl; pyrazolyl, particularly 3- and 5-pyrazolyl; pyrazinyl, particularly 2-pyrazinyl; pyridazinyl, particularly 3- and 4-pyridazinyl; pyridyl, particularly 2-, 3- and 4-pyridyl; pyrimidinyl, particularly 2- and 4-pyrimidinyl; quinoxalinyl, particularly 2- and 5-quinoxalinyl; quinolinyl, particularly 2- and 3-quinolinyl; 5-tetrazolyl; 2-thiazolyl; particularly 2-thiazolyl, 4-thiazolyl and 5-thiazolyl; thienyl, particularly 2- and 3-thienyl; and 3-(1,2,4-triazolyl). The aforementioned listing of heteroaryl moieties is intended to be representative, not limiting.

As used herein, "styryl sulfone" or "styryl sulfone compound" or "styryl sulfone therapeutic" referrers to chemical compounds containing one or more such styryl sulfone groups.

As used herein "dimethylamino($C_2$-$C_6$ alkoxy)" refers to $(CH_3)_2N(CH_2)_nO$— wherein n is from 2 to 6. Preferably, n is 2 or 3. Most preferably, n is 2, that is, the group is the dimethylaminoethoxy group, that is, $(CH_3)_2NCH_2CH_2O$—.

As used herein "sulfamyl" refers to the group —$SO_2NH_2$.

As used herein, "halo" or "halogen" includes fluorine, chlorine, bromine and iodine.

As used herein, "phosphate" and "phosphonate" and "phosphonato" refer to the moieties having the following structures:

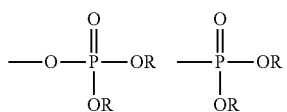

As used herein "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, alkyl, CN, $NO_2$, $CO_2R$, C(O)R, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3$R, —$SO_2$N(R')(R''), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, $CF_3$, $CO_2R$, C(O)R, C(O)$NR_2$, $NR_2$, $NO_2$, and OR.

With respect to the above definitions, each R is independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and a substituted and unsubstituted heterocyclic group. Each R' and R'' are independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and substituted and unsubstituted heterocyclic group; or R' and R'' may be taken together with the nitrogen to which they are attached to form a 5- to 7-membered ring which may optionally contain a further heteroatom. The substituted alkyl, substituted cycloalkyl, substituted cycloalkenyl, substituted alkenyl, substituted alkynyl, substituted aralkyl, substituted aryl and substituted heterocyclic group may be substituted with one or more of halo, CN, $CF_3$, OH, $CO_2H$, $NO_2$, $C_{1-6}$alkyl, —O—($C_{1-6}$alkyl), —$NH_2$, —NH($C_{1-6}$alkyl) and —N($C_{1-6}$alkyl)$_2$.

As used herein "heteroatom", particularly as a ring heteroatom, refers to N, O, and S. The inventor has now unexpectedly discovered that a radioprotective α,β-unsaturated aryl sulfone and specifically ON 01210.Na can be formulated very effectively as parenteral and oral compositions that are extraordinarily shelf stable without any noticeable degradation of the active entity.

The α,β-unsaturated aryl sulfones, in particular benzyl styryl sulfones, provide significant and selective systemic protection of normal cells from radiation-induced damage in animals. When used in radiotherapy techniques, these compounds also exhibit independent toxicity to cancer cells. Compositions and formulations of α,β-unsaturated aryl sulfone described herein protect normal cells and tissues from the effects of acute and chronic exposure to ionizing radiation. The α,β-unsaturated aryl sulfones are also operationally cytotoxic in tumor cells.

In one embodiment, compositions described herein are intended for prophylactic and/or treatment use. In another embodiment, the composition of this invention is used to enhance survival in personnel who are in imminent danger of exposure to life-threatening levels of x-ray or gamma radiation, and/or to enhance survival in personnel who have just received life-threatening levels of x-ray or gamma radiation. In animal efficacy studies, pre-treatment with ON.01210.Na, for example, by the intravenous, subcutaneous, intraperitoneal or oral route resulted in protection of mice from a lethal dose of ionizing radiation.

In yet another embodiment, subjects may be exposed to ionizing radiation when undergoing therapeutic irradiation for the treatment of proliferative disorders. Such disorders include cancerous and non-cancer proliferative disorders. Formulations described herein are effective in protecting normal cells during therapeutic irradiation of a broad range of tumor types, including but not limited to the following: breast, prostate, ovarian, lung, colorectal, brain (i.e., glioma) and renal. The compositions of this invention are also effective against leukemic cells, for example. The compositions are useful in protecting normal cells during therapeutic irradiation of abnormal tissues in non-cancer proliferative disorders, including but not limited to hemangiomatosis in new born, secondary progressive multiple sclerosis, chronic progressive myelodegenerative disease, neurofibromatosis, ganglioneuromatosis, keloid formation, Paget's Disease of the bone, fibrocystic disease of the breast, Peronies and Duputren's fibrosis, restenosis and cirrhosis, among others.

Therapeutic ionizing radiation may be administered to a subject on any schedule and in any dose consistent with the prescribed course of therapy (e.g., treatment and/or prevention) The course of therapy differs from subject to subject, and those of ordinary skill in the art can readily determine the appropriate dose and schedule of therapeutic radiation in a given clinical situation. Compositions of α,β-unsaturated aryl sulfone described herein may be administered far enough in advance of the radiation whether anticipated, planned or inadvertent, concomitant with exposure to radiation, and/or after exposure to radiation such that the compound is able to reach the normal cells of the subject in sufficient concentration to exert a radioprotective/mitigative effect on the normal cells. At least one α,β-unsaturated aryl sulfone may be administered as much as about 24 hours prior to or after the administration of the radiation. In one embodiment, an α,β-unsaturated aryl sulfone formulation is administered at least about 6-24 hours before exposure to radiation. Most preferably, the α,β-unsaturated aryl sulfone is administered once at about 24 hours and again at about 15 minutes before the radiation exposure. Alternatively, it could be administered once 24 hours and again at about 48 hours post radiation. One or more α,β-unsaturated aryl sulfones may be administered simultaneously, or different α,β-unsaturated aryl sulfones may be administered at different times during the therapy.

In one embodiment, about 24 hour period separates administration of α,β-unsaturated aryl sulfone and the therapeutic radiation. In another embodiment, the administration of α,β-unsaturated aryl sulfone and the therapeutic radiation is separated by about 6 to 18 hours. This strategy will yield significant reduction in radiation-induced side effects without affecting the anticancer activity of the therapeutic radiation.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

In the event of a terrorist attack releasing lethal amounts of radiation, radio-protective compositions described herein should provide protection when administered prior to, concomitant with and/or just after, e.g., up to about four hours after, exposure.

According to one embodiment, the α,β unsaturated aryl sulfone group is a styryl sulfone group:

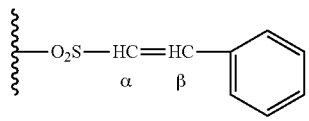

wherein the hydrogen atoms attached to the α and β carbons are optionally replaced by other chemical groups, and the phenyl ring is optionally substituted.

The α,β unsaturated aryl sulfone radioprotective compounds are characterized by cis-trans isomerism resulting from the presence of a double bond. Stearic relations around a double bond are designated as "Z" or "E". Both configurations are included in the scope of "α,β unsaturated aryl sulfone":

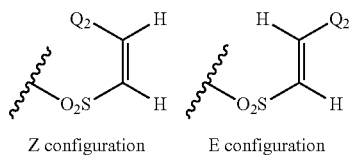

Z configuration        E configuration

According to one embodiment, the α,β unsaturated aryl sulfone compound is a compound of the formula I:

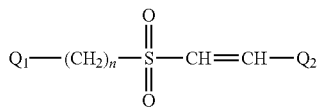

wherein:
n is one or zero;
$Q_1$ and $Q_2$ are, same or different, are substituted or unsubstituted aryl, or substituted or unsubstituted heteroaryl.

Preferably, n in formula I is one, that is, the compounds comprise α,β unsaturated benzylsulfones, e.g. styryl benzylsulfones.

In one preferred embodiment according to formula I, $Q_1$ and/or $Q_2$ are selected from substituted and unsubstituted heteroaryl; for example, (E)-3-furanethenyl-2,4-dichlorobenzylsulfone.

In another preferred embodiment according to formula I, $Q_1$ and $Q_2$ are selected from substituted and unsubstituted phenyl.

Preferred compounds where $Q_1$ and $Q_2$ are selected from substituted and unsubstituted phenyl comprise compounds of the formula II:

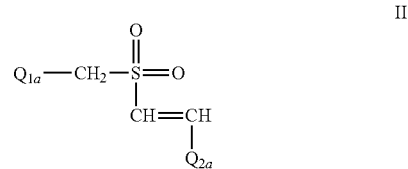

wherein:
$Q_{1a}$ and $Q_{2a}$ are independently selected from the group consisting of phenyl and mono-, di-, tri-, tetra- and penta-substituted phenyl where the substituents, which may be the same or different, are independently selected from the group consisting of hydrogen, halogen, $C_1$-$C_8$ alkyl, $C_1$-$C_8$ alkoxy, nitro, cyano, carboxy, hydroxy, phosphonato, amino, sulfamyl, acetoxy, dimethylamino($C_2$-$C_6$ alkoxy), $C_1$-$C_6$ trifluoroalkoxy and trifluoromethyl.

In one embodiment, compounds of formula II are at least di-substituted on at least one ring, that is, at least two substituents on at least one ring are other than hydrogen. In another embodiment, compounds of formula II are at least trisubstituted on at least one ring, that is, at least three substituents on at least one ring are other than hydrogen.

In one embodiment, the radioprotective compound has the formula III:

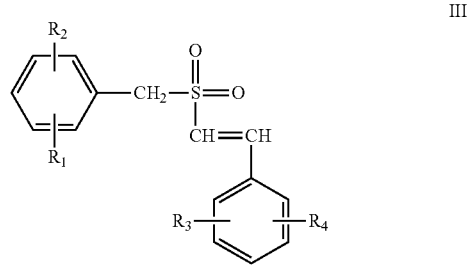

wherein $R_1$, $R_2$, $R_3$ and $R_4$ are independently selected from the group consisting of hydrogen, halogen, $C_1$-$C_8$ alkyl, $C_1$-$C_8$ alkoxy, nitro, cyano, carboxy, hydroxy phosphonato, amino, sulfamyl, acetoxy, dimethylamino($C_2$-$C_6$ alkoxy), $C_1$-$C_6$ trifluoroalkoxy and trifluoromethyl.

According to a particularly preferred embodiment of the invention, the radioprotective compound is according to formula III, and $R_1$ and $R_2$ are independently selected from the group consisting of hydrogen, halogen, cyano, and trifluoromethyl; and $R_3$ and $R_4$ are independently selected from the group consisting of hydrogen and halogen.

According to one sub-embodiment of formula III, the radioprotective α,β unsaturated aryl sulfone compound is a compound of the formula IIIa, wherein $R_2$ and $R_4$ are other than hydrogen:

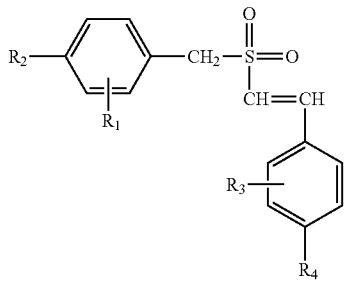

IIIa

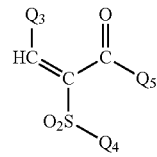

V wherein $Q_3$, $Q_4$ and $Q_5$ are independently selected from the group consisting of phenyl and mono-, di-, tri-, tetra- and penta-substituted phenyl where the substituents, which may be the same or different, are independently selected from the group consisting of halogen, $C_1$-$C_8$ alkyl, $C_1$-$C_8$ alkoxy, nitro, cyano, carboxy, hydroxy, amino, sulfamyl, acetoxy, dimethylamino($C_2$-$C_6$ alkoxy), $C_1$-$C_6$ trifluoroalkoxy and trifluoromethyl.

According to one sub-embodiment of formula V, the radioprotective α,β unsaturated aryl sulfone compound is a compound of the formula Va:

Preferred compounds according to formula Ma having the E-configuration include, but are not limited to, (E)-4-fluorostyryl-4-chlorobenzylsulfone; (E)-4-chlorostyryl-4-chlorobenzylsulfone; (E)-2-chloro-4-fluorostyryl-4-chlorobenzylsulfone; (E)-4-carboxystyryl-4-chlorobenzyl sulfone; (E)-4-fluorostyryl-2,4-dichlorobenzylsulfone; (E)-4-fluorostyryl-4-bromobenzylsulfone; (E)-4-chlorostyryl-4-bromobenzylsulfone; (E)-4-bromostyryl-4-chlorobenzylsulfone; (E)-4-fluorostyryl-4-trifluoromethylbenzylsulfone; (E)-4-fluorostyryl-3,4-dichlorobenzylsulfone; (E)-4-fluorostyryl-4-cyanobenzylsulfone; (E)-2,4-dichloro-4-chlorobenzylsulfone; (E)-4-fluorostyryl-4-chlorophenylsulfone and (E)-4-chlorostyryl-2,4-dichlorobenzylsulfone.

According to another embodiment, compounds of formula Ma have the Z configuration wherein $R_1$ and $R_3$ are hydrogen, and $R_2$ and $R_4$ are selected from the group consisting of 4-halogen. Such compounds include, for example, (Z)-4-chlorostyryl-4-chlorobenzylsulfone; (Z)-4-chlorostyryl-4-fluorobenzylsulfone; (Z)-4-fluorostyryl-4-chlorobenzylsulfone; (Z)-4-bromostyryl-4-chlorobenzylsulfone; and (Z)-4-bromostyryl-4-fluorobenzylsulfone.

According to another embodiment, the radioprotective α,β unsaturated aryl sulfone compound is a compound of the formula IV:

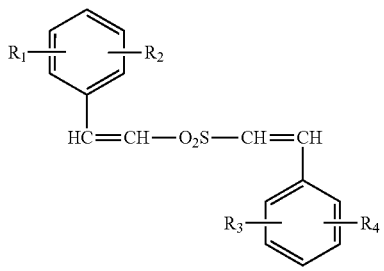

IV wherein $R_1$, $R_2$, $R_3$, and $R_4$ are independently selected from the group consisting of hydrogen, halogen, $C_{1-8}$ alkyl, $C_{1-8}$ alkoxy, nitro, cyano, carboxy, hydroxy, alkoxy, and trifluoromethyl.

In one embodiment, $R_1$ in formula IV is selected from the group consisting of hydrogen, chlorine, fluorine and bromine; and $R_2$, $R_3$ and $R_4$ are hydrogen. An embodiment of compound of formula IV is (Z)-styryl-(E)-2-methoxy-4-ethoxy-styrylsulfone.

According to yet another embodiment, the radioprotective α,β unsaturated aryl sulfone compound is a compound of the formula V:

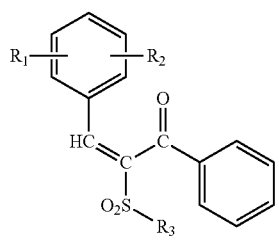

Va wherein $R_1$ and $R_2$ are independently selected from the group consisting of hydrogen, halogen, $C_1$-$C_8$ alkyl, $C_1$-$C_8$ alkoxy, nitro, cyano, carboxyl, hydroxyl, and trifluoromethyl; and $R_3$ is selected from the group consisting of unsubstituted phenyl, mono-substituted phenyl and di-substituted phenyl, the substituents on the phenyl ring being independently selected from the group consisting of halogen and $C_1$-$C_8$ alkyl.

Preferably, $R_1$ in formula Va is selected from the group consisting of fluorine and bromine; $R_2$ is hydrogen; and $R_3$ is selected from the group consisting of 2-chlorophenyl, 4-chlorophenyl, 4-fluorophenyl, and 2-nitrophenyl.

A preferred radioprotective styryl sulfone according to formula Va is the compound wherein $R_1$ is fluorine, $R_2$ is hydrogen and $R_3$ is phenyl, that is, the compound 2-(phenylsulfonyl)-1-phenyl-3-(4-fluorophenyl)-2-propen-1-one.

Where a substituent on an aryl nucleus is an alkoxy group, the carbon chain may be branched or straight, with straight being preferred. Preferably, the alkoxy groups comprise $C_1$-$C_6$ alkoxy, more preferably $C_1$-$C_4$ alkoxy, most preferably methoxy.

In another preferred embodiment of the invention, $R_1$ and $R_3$ are hydrogen, $R_2$ is chlorine and $R_4$ is carboxy and the stearic configuration around the double bond is E, e.g. (E)-4-carboxystyryl-4-chlorobenzylsulfone (ON 01210.Na).

The α,β-unsaturated aryl sulfones may take the form or pharmaceutically acceptable salts. The term "pharmaceutically acceptable salts" embraces salts commonly used to form alkali metal salts and to form addition salts of free acids or free bases. A preferred salt useful in the formulation is the sodium salt (ON 01210.Na). Polymorphs of ON 01210.Na, as specifically discussed infra, is intended to be within the scope of the claims appended hereto.

(E)-α,β-unsaturated aryl sulfones may be prepared by Knoevenagel condensation of aromatic aldehydes with benzylsulfonyl acetic acids or arylsulfonyl acetic acids. The procedure is described by Reddy et al., Acta. Chim. Hung. 115: 269-71 (1984); Reddy et al., Sulfur Letters 13:83-90 (1991); Reddy et al., Synthesis No. 4, 322-23 (1984); and Reddy et al., Sulfur Letters 7:43-48 (1987), the entire disclosures of which are incorporated herein by reference. See, particularly, the entire disclosure of U.S. Pat. No. 6,667,346.

An exemplary species of a radioprotective α,β-unsaturated aryl sulfone is ON 01210.Na. ON 01210.Na is a derivative of chlorobenzylsulfone. This compound is described in U.S. Pat. Nos. 6,656,973 and 6,667,346 as exhibiting valuable prophylactic properties which mitigate the effects of accidental and intentional exposure to life-threatening levels of irradiation. Hence, a systematic development of this compound is described with the objective of developing a shelf stable formulation.

Table 1 describes the general physical properties of ON. 1210.Na. The exemplary compound is a sodium salt of (E)-4-Carboxystyryl-4-chlorobenzylsulfone.

TABLE 1

Physical Properties of ON.1210.Na

| Chemical Structure | [structure image] |
|---|---|
| Chemical Name | (E)-4-Carboxystyryl-4-chlorobenzylsulfone, Sodium Salt |
| Empirical Formula | $C_{16}H_{12}ClNaO_4S$ |
| Molecular Weight | 358.79 |
| Physical Nature | White crystalline flakes |
| Melting Point | 354-356° C. |
| Solubility | Soluble in water at 8-10 mg/ml |

The compound ON 01210.Na appears to form at least one polymorph. X-ray diffraction pattern, for example, of precipitated ON 01210.Na is different from that of the originally synthesized compound. Polymorphs of ON 01210.Na are intended to be within the scope of the claims appended hereto.

Figure 2:
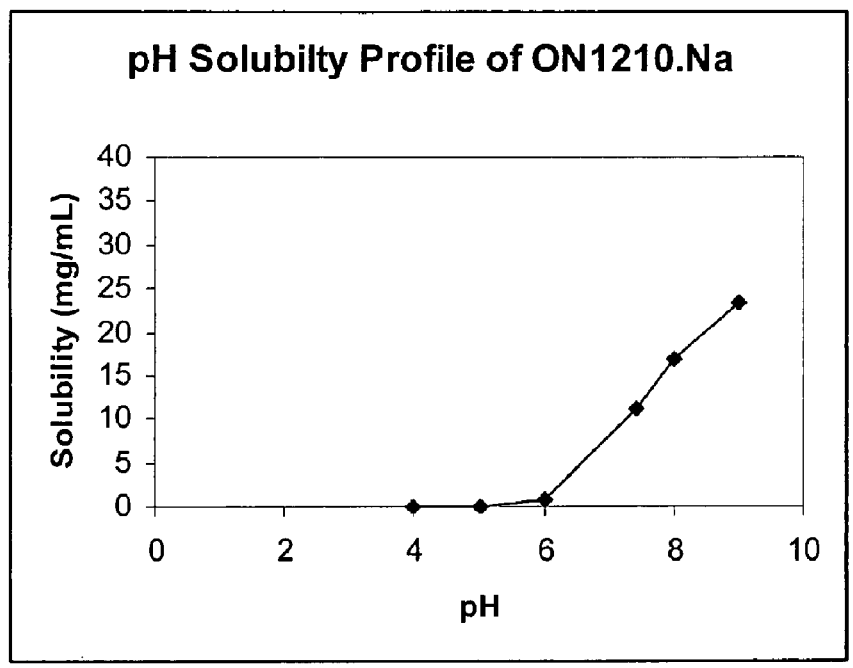
FIG. 2 shows pH solubility profiles of ON 01210.Na at ambient temperature.
Figure 3A:
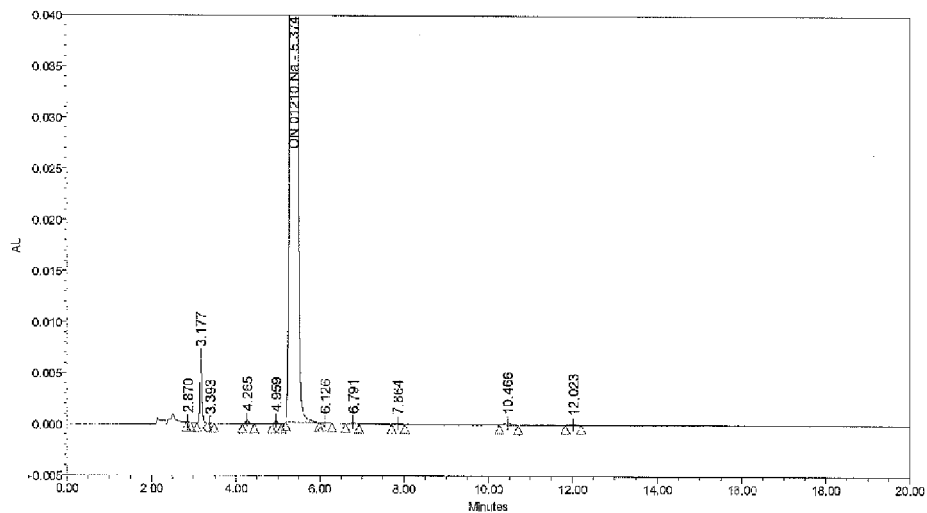
FIG. 3 shows stability profiles of ON 01210.Na formulation without TPGS at ambient temperature (25° C.) and 60% relative humidity at T=0 and 3 months and at 40° C. and 75% relative humidity at T=3 months.
Figure 3A:
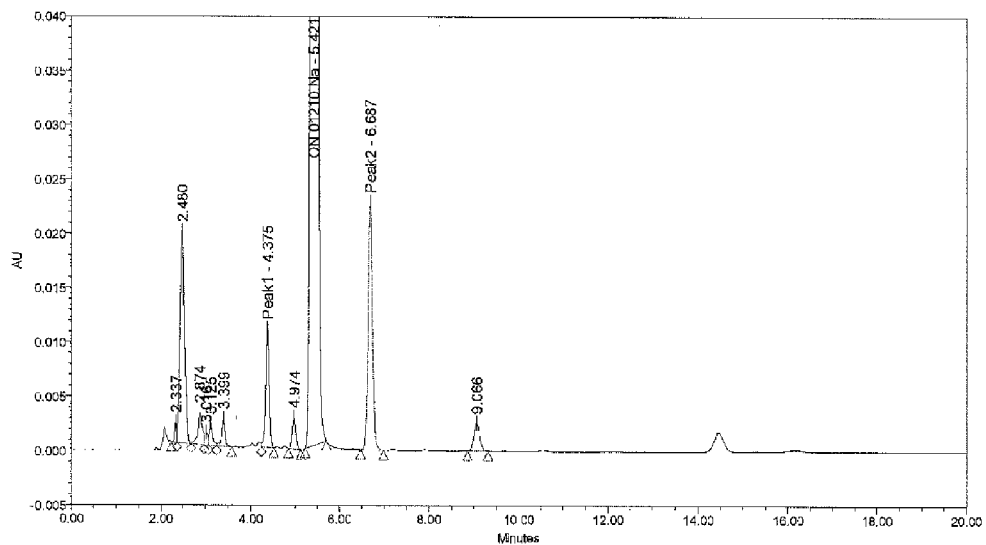
Figure 3B:
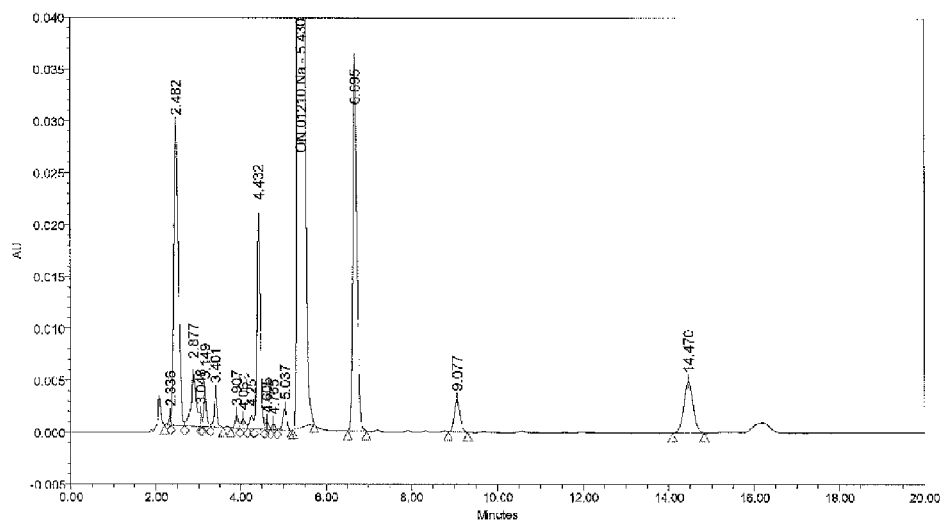
Figure 4A:
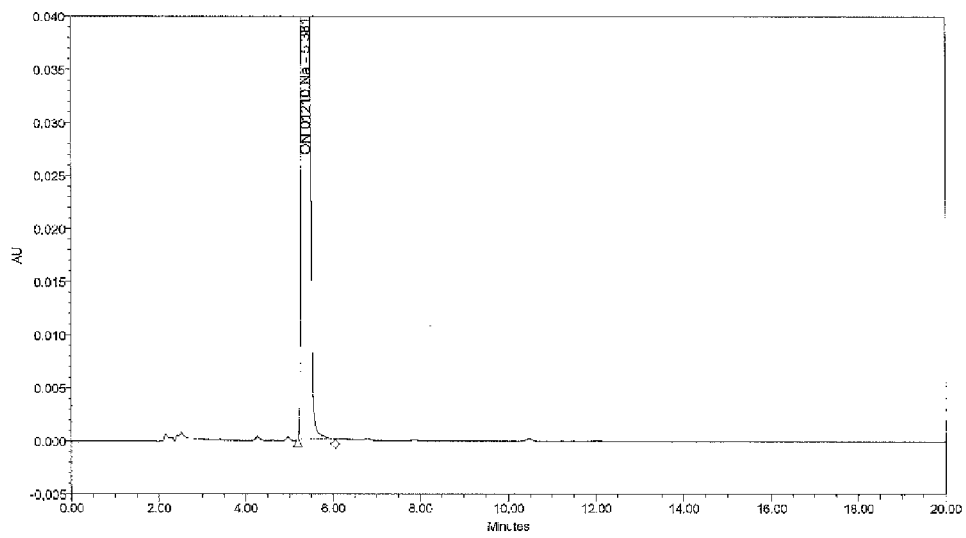
FIGS. 4A-4B shows stability profiles of ON 01210.Na formulation with TPGS at ambient temperature. (25° C.) and 60% relative humidity at T=0 and 3 months and at 40° C. and 75% relative humidity at T=3 months.
Figure 4A:
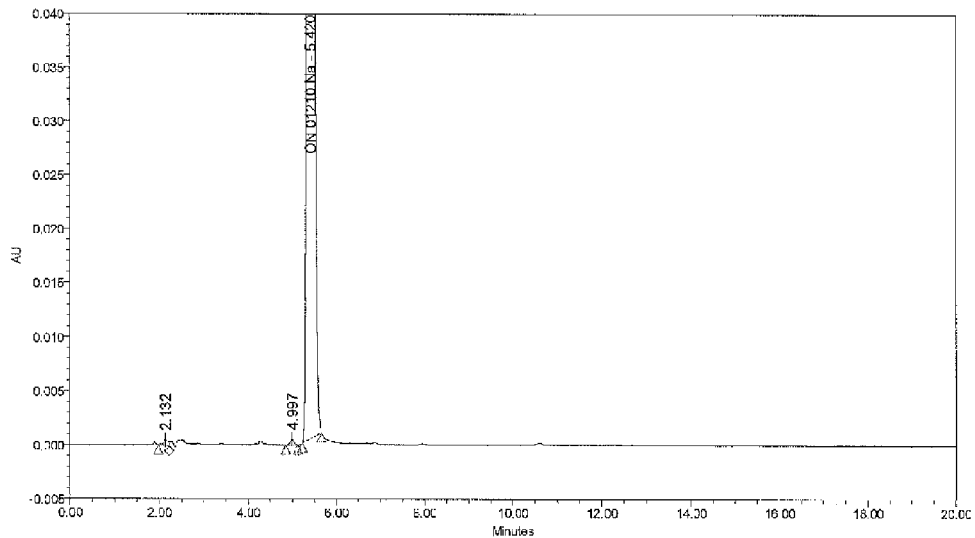
Figure 4B:
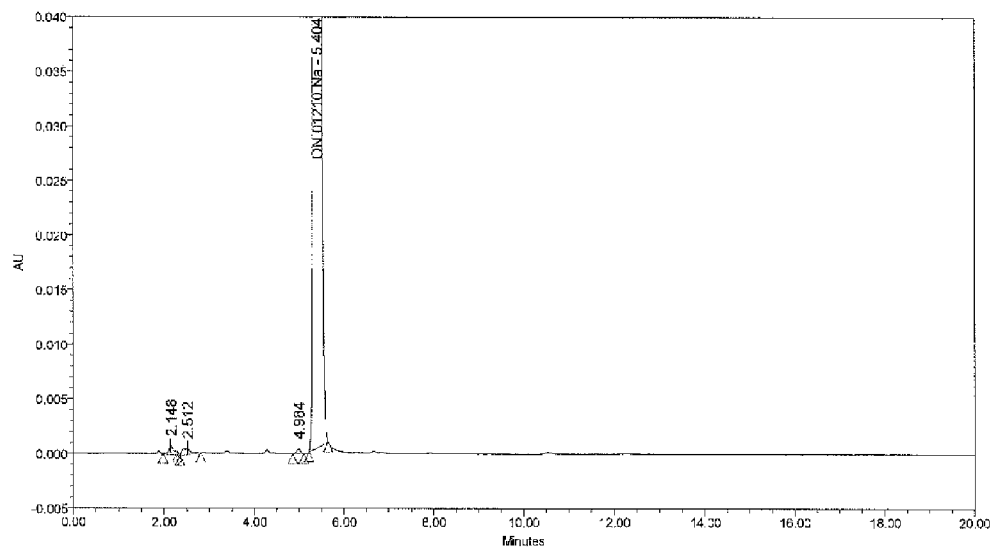

The physio-chemical properties of ON 01210.Na, as an exemplary efficacious radiation protectant drug, were determined in order to evaluate appropriate formulation approaches for development of a safe, reliable and effective parenteral formulation of this compound and other radioprotective α,β-unsaturated arylsulfones. Evaluation studies included microscopic studies, partition coefficient, pKa, pH solubility studies, pH stability studies under accelerated conditions, solid state characterization of the drug substance, and solid state stability of drug substance under accelerated conditions. The preformulation studies showed that the compound had a low octanol:water partition coefficient (1.28-2.87). The equilibrium solubility of the drug at pH 4.0, 5.0, 6.0, 7.4, 8.0, 9.0 was 0.000154, 0.0379, 0.715, 11.09, 16.81, 23.3 mg/ml, respectively (FIG. 2). The pKa calculated from pH-solubility studies was 2.85.+−.0.6. The pH-stability profile of the drug indicated better stability at neutral and biological pH but degradation was rapid under acidic conditions. The degradation followed a pseudo-first-order rate. The accelerated solid-state stability study of the bulk drug substance showed no evidence of degradation. This drug was reasonably stable in an aqueous environment at biological pH. Therefore, it was determined that ON 01210.Na could be formulated as a shelf stable parenteral formulation. It was found that the aqueous solubility of the drug as the free acid was low and could be significantly enhanced by increase in pH, co-solvents and complexation.

The invention as disclosed and described herein provides shelf stable aqueous formulations that are stabilized with a stabilizing agent that is capable of reduction and/or prevention of nucleophilic conjugate addition products. The invention makes use of at least one stabilizing agent that helps prevent the degradation of the active moiety and eventual precipitation of the conjugate addition product. The stabilizing agent within the scope of the invention includes, by way of example and not limitation, water soluble Vitamin E derivatives, including Vitamin E TPGS, Tocopheryl succinate, 6-Hydroxy-2,5,7,8-tetramethylchroman-2-carboxylic Acid (Trolox), tocopherol monoglucoside (TMG) and the like.

Certain derivatives of compounds of formula (I-V) which may have little or no pharmacological activity themselves can, when administered into or onto the body, be converted into compounds of formula (I-V) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

In one embodiment, the prodrug is a compound that is transformed in vivo to yield a compound of Formula (I-V) or a pharmaceutically acceptable salt or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Prodrugs in accordance with the invention can, for example, be produced by replacing appropriate functionalities present in the compounds of Formula (I-V) with certain moieties known to those skilled in the art as 'pro-moieties' as described, for example, in "Design of Prodrugs" by H Bundgaard (Elsevier, 1985).

Moreover, certain compounds of Formula (I-V) may themselves act as prodrugs of other compounds of Formula (I-V).

A prodrug of a compound of Formula (I-V) may be one formed in a conventional manner with a functional group of the compound, such as with an amino, hydroxy or carboxy group.

For example, if a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural alpha-aminoacyl or natural alpha-aminoacyl-natural alpha-aminoacyl, —CH(OH)C(O)OY' wherein Y' is H, ($C_1$-$C_6$)alkyl or benzyl, —C(OY$_0$)Y$_1$ wherein Y$_0$ is ($C_1$-$C_4$) alkyl and Y$_1$ is ($C_1$-$C_6$)alkyl, carboxy($C_1$-$C_6$)alkyl, amino ($C_1$-$C_4$)alkyl or mono-N— or di-N,N—($C_1$-$C_6$)alkylamino alkyl, —C(Y$_2$)Y$_3$ wherein $Y_2$ is H or methyl and $Y_3$ is mono-N— or di-N,N—($C_1$-$C_6$)alkylamino, morpholino, piperidin-1-yl or pyrrolidin-1-yl.

Similarly, if a compound of the present invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, .alpha.-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1$-$C_6)$ alkyl$)_2$ or glycosyl.

If a compound of the present invention contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as beta-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Also included within the scope of the invention are metabolites of compounds of Formula (I-V) that are compounds formed in vivo upon administration of the drug. Some examples of metabolites in accordance with the invention include: (i) where the compound of Formula (I-V) contains a methyl group, an hydroxymethyl derivative thereof (—$CH_3$→$CH_2OH$); (ii) where the compound of Formula (I-V) contains a tertiary amino group, a secondary amino derivative thereof (—$NR^1R^2$→—$NHR^1$ or →—$NHR^2$); (iii) where the compound of formula (I) contains a secondary amino group, a primary derivative thereof (—$NHR^1$→—$NH_2$); (iv) where the compound of Formula (I-V) contains a phenyl moiety, a phenol derivative thereof (-Ph→-PhOH); and (v) where the compound of Formula (I-V) contains an amide group, a carboxylic acid derivative thereof.

Further examples of replacement groups in accordance with the foregoing examples and examples of other prodrug types in accordance with the invention may be found in the aforementioned references.

Compounds of the invention may exist in various hydrated forms. For example, the compounds of the present invention may exist in insolated as well as solvated forms with pharmaceutically acceptable solvents such as water, ethanol, and the like, and it is intended that the invention embrace both solvated and insolated forms.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs. Alternatively, the compounds of the invention may be in an amorphous state The present invention also embraces isotopic ally-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$, and $^{36}Cl$, respectively.

Certain isotopic ally-labeled compounds of the present invention (e.g., those labeled with $^3H$ and $^{14}C$) are useful in compound and/or substrate tissue distribution assays. Triturated (i.e., $^3H$) and carbon-14 (i.e., $^{14}C$) isotopes are particularly preferred for their ease of preparation and detestability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopic ally labeled compounds of the present invention can generally be prepared by following procedures analogous to those disclosed in the Schemes and/or in the Examples herein below, by substituting an isotopic ally labeled reagent for a non-isotopic ally labeled reagent.

When one or more chiral centers are present in the compounds of the present invention, the individual isomers and mixtures thereof (e.g., racemates, racemic mixtures, individual diastereomers or enantiomers, etc.) are intended to be encompassed by the formulae depicted herein. Thus, for example, the exemplified compounds disclosed herein are depicted as specific stereoisomers. It should be understood that the present invention includes such compounds but having alternate stereochemistry at one or more of the chiral centers.

In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

In certain embodiments, compounds of the invention may exist in several tautomeric forms. Accordingly, the chemical structures depicted herein encompass all possible tautomeric forms of the illustrated compounds. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Pharmaceutical Composition Formulation, Dosage and Mode of Administration

The present invention also provides pharmaceutical compositions comprising a therapeutically effective amount of an α,β-unsaturated aryl sulfone compound, and a pharmaceutically acceptable carrier. The pharmaceutical composition also refers to a composition that additionally contains one or more active or inactive agents.

According to one embodiment, the α,β-unsaturated aryl sulfone of the invention having radioprotection activity as described are provided as isolated and substantially purified compounds in pharmaceutically acceptable formulations. These formulations can be administered by standard routes.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Water is a preferred carrier when the pharmaceutical composition is administered orally and/or parenterally. Saline solutions and aqueous dextrose and glycerol solutions can also be employed as liquid carriers, particularly for injectable solutions.

In a preferred embodiment, the compositions described herein, are aqueous-based. The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, Isopropylamine, triethylamine, 2-ethylaminoethanol, histidine, procaine, etc.

The preferred routes of administration of the compositions described herein include, for example, parenteral, and oral administration. Parenteral administration includes intravenous, intramuscular, intraarterial, intraperitoneal, intravaginal, intravesical (e.g., into the bladder), intradermal, intracranial, intratracheal and epidural) administration. The α,β-unsaturated aryl sulfone, ON 01210.Na, may be administered in the form of a pharmaceutical composition comprising ON 01210.Na in combination with at least one stabilizing agent and a pharmaceutically acceptable carrier. ON 01210.Na in such formulations may comprise from 0.1 to 99.99 weight percent. By "pharmaceutically acceptable carrier" is meant any carrier, diluent or excipient, for example a water soluble polymer/cosolvent, which is compatible with the other ingredients of the formulation and is not deleterious to the subject.

Formulations suitable for parenteral administration include aqueous injection solutions which may contain antioxidants, buffers, bacteriostats and solutes which render the formulation isotonic with the blood of the intended recipient. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions may be prepared from sterile powders.

The pharmaceutical composition formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both.

The compounds or compositions may be administered together with other biologically active agents. Administration can be systemic or local. In addition, it may be desirable to introduce the pharmaceutical compounds or compositions of the invention into the central nervous system by any suitable route, including intrathecal and intraventricular injection that may be facilitated by an intraventricular catheter, for example, attached to a reservoir, such as an Ommaya reservoir. Pulmonary administration can also be employed, i.e., by use of an inhaler or nebulizer, and formulation with an aerosolizing agent.

In a specific embodiment, it may be desirable to administer the pharmaceutical compounds or compositions of the invention locally to the area in need of radiation prevention and/or treatment; this may be achieved by, for example, and not by way of limitation, local infusion, topical application, i.e., in conjunction with a wound dressing after surgery, by injection or by means of a catheter.

The amount of the compound of the invention which will be effective in the treatment, inhibition and prevention of toxicity induced radiation can be determined by standard clinical techniques. In addition, in vitro assays may optionally be employed to help identify optimal dosage ranges.

In particular, the dosage of the composition of the present invention will depend on clinical factors such as weight and condition of the human or animal and the route of administration of the compound. The precise dose to be employed in the formulation, therefore, should be decided according to the judgment of the practitioner and each patient's circumstances. Effective doses may be extrapolated from dose-response curves derived from in vitro or animal model test systems.

For treating humans or animals, between approximately 0.5 to 500 mg/kilogram is typical broad range for administering the pharmaceutical composition of the invention. The methods of the present invention contemplate single as well as multiple administrations, given either simultaneously or over an extended period of time. It is to be understood that the present invention has application for both human and veterinary use.

The specific dose and schedule of α,β-unsaturated aryl sulfone to obtain the radioprotective benefit will, of course, be determined by the particular circumstances of the individual patient including, the size, weight, age and sex of the patient, the nature and stage of the disease being treated, the aggressiveness of the disease, and the route of administration, and the specific toxicity of the radiation. For example, a daily dosage of from about 0.01 to about 150 mg/kg/day may be utilized, more preferably from about 0.05 to about 100 mg/kg/day. Particularly preferred are doses from about 1.0 to about 50.0 mg/kg/day, for example, a dose of about 10.0 mg/kg/day. The dose may be given over multiple administrations, for example, two administrations of 5 mg/kg. Higher or lower doses are also contemplated.

The term "effective amount" of ON 01210.Na as used herein refers to an amount after dilution that is effective to mitigate, reduce or eliminate toxicity associated with radiation in normal cells of the subject and/or to impart a direct cytotoxic effect to abnormally proliferating cells in the subject. ON 01210.Na is administered, for example, in a concentration of about 0.25 micromolar to about 100 micromolar; preferably, from about 1.0 to about 50 micromolar; more preferably from about 2.0 to about 25 micromolar. Particularly preferred concentrations for administration are, for example, about 0.5, 1.0 and 2.5 micromolar and about 5, 10 and 20 micromolar. Higher or lower concentrations may also be used depending upon factors well known in the art.

According to a preferred embodiment, the α,β-unsaturated aryl sulfone, ON 01210.Na, is administered in the form of a pharmaceutical composition comprising ON 01210.Na in combination with at least one stabilizing agent and a pharmaceutically acceptable carrier. ON 01210.Na in such formulations may comprise from 0.1 to 99.99 weight percent. By "pharmaceutically acceptable carrier" is meant any carrier, diluent or excipient, for example a water soluble polymer/cosolvent, which is compatible with the other ingredients of the formulation and is not deleterious to the subject.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

A single dosage is generally within the range of about 1 ml to about 5 ml of any of the compositions described herein. Individual 3 ml dosages of compositions described herein are contemplated, for example. The dosages may be packaged, for example, in 5 ml vials.

The shelf stable formulation may also be filled in a self-injecting device for ease of use by individuals for reducing toxic effects of ionizing radiation. Such a device will deliver a pre-determined dose (or doses) of ON 01210.Na.

For parenteral administration, the $\alpha,\beta$-unsaturated aryl sulfone ON 01210.Na may be diluted, prior to parenteral administration, with a suitable diluents selected from water, saline solution, aqueous dextrose (glucose) and related sugar solutions, propylene glycol or polyethylene glycol. Stabilizing agents, antioxidizing agents, chelating agents, and preservatives, for example, may also be added. Stabilizing agents are preferred and water soluble Vitamin E derivatives are most preferred. Suitable antioxidizing agents include sulfite, ascorbic acid, citric acid and its salts, and sodium EDTA as a chelator, for example. Suitable preservatives include benzalkonium chloride, methyl- or propyl-paraben, and chlorbutanol.

The formulations described and claimed herein are generally intended for parenteral as well as oral administration. Compositions of the present invention are generally formulated with active ingredient, e.g., ON 01210.Na, with a stabilizing agent and a cosolvent buffered at about pH between 7.0 and 8.7. Preferred compositions of the present invention comprise between about 5 mg/ml to about 200 mg/ml of ON 01210.Na in an aqueous solution. More preferred shelf-stable compositions of the present invention, for dilution prior to administration, generally comprise between about 10 mg/ml to about 150 mg/ml of ON 01210.Na. These shelf stable formulations are useful for oral and parenteral administration. Most preferred parenteral administration is by the subcutaneous route. Intramuscular administration is also preferred. For intravenous administration, if desired, these compositions may be diluted with a suitable parenteral diluent prior to infusion. Compositions of the present invention may, for example, be diluted with about 7 parts diluent (7:1) prior to intravenous administration. However, the dilution factor and the diluent employed depend on the concentration of drug in the formulation. Compositions of the present invention, however, may be diluted with anywhere, for example, within the range of about 2 volumes of suitable parenteral diluent prior to infusion to about 12 volumes of suitable parenteral diluent, prior to intravenous administration. Preferred compositions of the present invention comprise between about 5 mg/ml to about 200 mg/ml of ON 01210.Na in an aqueous solution.

In one embodiment, the compositions of the present invention for intravenous administration have a pH within the range of about 7.0 to about 9.5 A diluted product pH of about 7.0 to about 8.0 is preferred. The osmolarity of the diluted formulation for parenteral administration should be approximately within the range of about 200 to about 400 mOsm/kg. Preferred osmolarity of the diluted formulation for administration should be approximately within the range of about 270 to about 330 mOsm/kg. A preferred osmolarity of the diluted formulation for administration should be approximately 300 mOsm/kg.

Example compositions of the present invention comprise between about 20 mg/ml to about 150 mg/ml (e.g., about 25 mg/ml, 50 mg/ml, 75 mg/ml, 100 mg/ml, 125 mg/ml, 150 mg/ml) of at least one $\alpha,\beta$-unsaturated aryl sulfone (e.g., (E)-4-carboxystyryl-4-chlorobenzylsulfone sodium salt (ON 01210.Na)); wherein the composition exhibits a pH within the range of about 7 to about 10. A preferred pH, for example, is between about 8 and about 9, for example. A pH between about 8.3 and about 8.7 is preferred, for example. About 8.5 is an example preferred pH (between about 8.4 and about 8.6). Most preferred buffer is Tris-EDTA, for example, which provides a good physiological buffering capacity at the pH of administration. Exemplary compositions of the present invention described herein exhibit a final concentration of about 0.2M Tris and 0.02M EDTA. However, the Tris concentration may be within a range of about 0.005 M to about 0.5 M (or about 0.005M to about 0.5M "Tris-EDTA", for example) to suit the conditions for administration. Any buffer known in the art to be suitable for injectable formulations may be employed in these compositions of the present invention. Suitable buffering agents, for example, include phosphate buffers, for example, trisodium orthophosphate, disodium hydrogen phosphate, sodium bicarbonate, as well as sodium citrate, potassium citrate, N-methylglucamine, L(+) lysine, glycine and L(+) arginine provide good buffering capacity between about pH 7-9.5, for example.

An example solution composition of the present invention comprises an effective amount of ON 01210.Na in a formulation which comprises between about 10 mg/ml to about 100 mg/ml of the compound (e.g., ON 01210.Na); at least one buffer selected from the group consisting of Tris-EDTA, sodium bicarbonate, sodium citrate, N-methylglucamine, L(+) lysine, glycine, L(+) arginine, and phosphate; a water-soluble cosolvent within the range of about 20% w/v to about 60% w/v; a stabilizing agent within the range of about 0.1% w/v to about 10% w/v, and, wherein the composition has a pH within the range of about 8 to about 9. An example composition of the present invention of this type comprises Tris-EDTA buffer within the range of about 0.005M-0.5M; PEG within the range of about 40% w/v to about 60% w/v; Vitamin E TPGS within the range of about 0.25% w/v to about 5% w/v, and, wherein the composition has a pH within the range of about 8.3 to about 8.7 A preferred example of this type comprises Tris-EDTA buffer within the range of about 0.1M to about 0.3M (e.g., 0.2M); PEG 400 within the range of about 40% w/v to about 60% w/v (e.g., 50% w/v); Vitamin E TPGS within the range of about 0.5% w/v to about 2.5% w/v (e.g., 1% w/v), and, wherein the composition has a pH within the range of about 8.3 to about 8.7 (e.g., between about 8.4 and about 8.6).

Another example composition of the present invention comprises about 20 mg/ml to about 60 mg/ml of the compound (ON 01210.Na); Tris-EDTA buffer within the range of about 0.15M to about 0.25M; PEG 400 within the range of about 45% w/v to about 55% w/v; Vitamin E TPGS within the range of about 0.5% w/v to about 2.5% w/v and, wherein the composition has a pH within the range of about 8.4 to about 8.6, and the compound is substantially stable in the composition at from about 25° C. to about 40° C. for at least about 120 days.

Formulations described herein are preferred which have a pH within a range of about 7.5 to about 9.2. High pH, e.g., about 8.5, is preferred. Compositions are preferred that comprise between about 0.5% and about 90% of at least one cosolvent, e.g. at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, and at least about 90%. The term "cosolvent", as used herein, includes but is not limited to water soluble excipients known in the art including water soluble polymers such as polyethylene glycol (PEG) (e.g., PEG 400), polypropylene glycol, and polyglycerol, DMA, propylene glycol, glycerol, ethanol, sorbitol, and isopropyl alcohol.

The viscosity of the formulation, for example, may be adjusted using a suitable viscosity modifying agent, for example carboxy methyl cellulose or any of the similar excipients well known in the art. See, e.g., Handbook of Pharmaceutical Excipients, for example. The viscosity modifying agent will be biocompatible and suitable for parenteral administration. The concentration of the suspending agent could vary from 0.1 to 5%. The preferred amount is in the range of about 1%.

Pharmaceutical Kits

The invention also provides a pharmaceutical pack or kit comprising one or more containers filled with the pharmaceutical compositions of the invention. The ingredients of the pharmaceutical compositions are about 20 mg/ml to about 100 mg/ml of at least one radioprotective α,β-unsaturated aryl sulfone and at least one cosolvent comprising a water soluble polymer including polyethylene glycol (PEG), polypropylene glycol, polyglycerol, DMA, propylene glycol, glycerol, ethanol, sorbitol, and isopropyl alcohol, or a combination thereof among others, in an amount between about 25% and about 90% w/v, and at least one stabilizing agent comprising a water soluble Vitamin E derivative including Vitamin E TPGS, Tocopheryl succinate, 6-Hydroxy-2,5,7,8-tetramethylchroman-2-carboxylic Acid (Trolox), and tocopherol monoglucoside (TMG), wherein the composition has a pH within the range of about 7.0 to about 9.5. Additionally provided in the kit is notice in the form prescribed by a governmental agency regulating the manufacture, use or sale of the pharmaceuticals, and an instruction for use of the pharmaceutical for human administration.

The following Examples serve to illustrate the invention without limiting the invention in its scope.

EXAMPLES

Example 1

Preparation of ON 01210.Na

4-Chlorobenzyl-4-carboxystyryl sulfone (ON 01210) (49 g; 0.145 mol) was taken in a one-liter conical flask and 500 ml of distilled water was added. Sodium hydroxide solution (16 ml: 10 M stock) (0.150 mol.) was added to the conical flask. The contents of the flask were then boiled with stirring till ON 01210 was completely dissolved. The solution was then cooled to room temperature and shining crystals separated were filtered through a fluted filter paper. The crystalline material was dried under vacuum to yield (48 g) (92% yield) of pure ON 1210.Na.

Example II

Preparation of ON 01210.Na Formulation A (without Vitamin E TPGS)

TRIS (968.0 mg), EDTA (233.8 mg), and deionized (DI) water (24 ml) were combined in a beaker equipped with a Teflon coated stirring bar. The mixture was stirred until complete dissolution occurred, and the resulting solution was covered with aluminum foil and allowed to stir gently overnight at room temperature. The following morning, PEG 400 NF (40.0 ml) was added to the TRIS/EDTA aqueous solution with continued stirring. The vessel containing PEG 400 NF was rinsed with DI water (2×3.2 ml), and the rinsate added to the formulation mixture. After stirring the mixture to homogeneity (approx. 10 minutes), the pH was measured to be 9.46 using a calibrated electronic pH meter. The pH was adjusted to 8.37 (target pH=8.40) by the careful addition of 98 pipet drops of 1.0 M HCl (aq) with stirring and allowed to fully equilibrate over a 10-15 minute period. Once the pH steadied at 8.37, ON 01210.Na (4.0 g) was added to the stirring formulation mixture. Complete dissolution required vigorous stifling and brief periodic sonication to break up ON 01210.Na clumps over a two hour period. After complete dissolution of ON 01210.Na, DI water (approx. 5 ml) was added to bring the final volume to approximately 80 milliliters. The pH of the resulting solution was determined to be 8.31, and thus 20 pipet drops of 1.0N NaOH(aq) were added to adjust the final formulation batch (defined as ON 01210.Na Formulation A) pH to 8.41-8.42. Formulation A was 0.22 micron filtered using a 100 ml Gastight Syringe equipped with a Millex®GP filter unit (Millipore Express® PES Membrane; Lot No R8KN13888).

Example III

Preparation of ON 01210.Na Formulation B (with Vitamin E TPGS)

TRIS (968.0 mg), EDTA (233.8 mg), and DI water (24 ml) were combined in a beaker equipped with a Teflon coated stirring bar. The mixture was stirred until complete dissolution, and then Vitamin E TPGS NF (800 mg) was added to the stirring mixture as a single heap (waxy solid slivers) and dissolution was completed with vigorous stirring and periodic brief sonication. The resulting "slurry" was covered with aluminum foil and allowed to stir gently overnight at room temperature. PEG 400 NF (40.0 ml) was added to the resulting TRIS/EDTA/Vitamin E TPGS aqueous solution with continued stifling. The vessel containing PEG 400 NF was rinsed with DI water (2×3.2 ml), and the rinsate added to the formulation mixture. After stifling the mixture to homogeneity (approx. 10 minutes), the pH was measured to be 9.36 using a calibrated electronic pH meter. The pH was adjusted to 8.38 (target pH=8.40) by the careful addition of 93 pipet drops of 1.0 M HCl (aq) with stirring. After the pH had steadied at 8.38, ON 01210.Na (4.0 g) was added to the stirring formulation mixture. Complete dissolution required vigorous stirring and brief periodic sonication to break up ON 01210.Na clumps over a two hour period. After complete dissolution of ON 01210.Na, DI water (approx. 5 ml) was added to bring the final volume to 80 milliliters. The pH of the final formulation batch (defined as ON 01210.Na Formulation B) was measured to be 8.40-8.41, and was not adjusted any further prior to 0.22 micron filtration using a 100 ml Gastight Syringe equipped with a Millex®GP filter unit (Millipore Express® PES Membrane; Lot No R8KN13888).

Example IV

Comparison of Formulations

The formulations prepared in Examples II (without TPGS) and III (with TPGS) were compared for their physical stability at 25° C. and 60% humidity by monitoring them over a six months period. Table 2 shows physical data for Formulation A of Example II in comparison to Table 3 comprising data for Formulation B of Example III at 25° C. and 60% humidity.

TABLE 2

| Formulation A (without TPGS)-25/60; ON 01210 Na (50 mg/ml) | | | | | | | |
|---|---|---|---|---|---|---|---|
| Test | Day 0 | Day 4 | Day 7 | Day 14 | Day 28 | Day 60 | Day 90 |
| Appearance-Color | Clear | Clear | Clear | Clear | Clear | Clear | Clear |
| Appearance-Particles | None | None | None | None | None | Fine | Fine |
| Ph | 8.40 | 8.33 | 8.33 | 8.24 | 8.20 | 8.03 | 7.92 |

TABLE 2-continued

Formulation A (without TPGS)-25/60; ON 01210 Na (50 mg/ml)

| Test | Day 0 | Day 4 | Day 7 | Day 14 | Day 28 | Day 60 | Day 90 |
|---|---|---|---|---|---|---|---|
| Assay (mg/ml) | 50.3 | 48.3 | 48.2 | 47.5 | 47.7 | 45.4 | 43.2 |
| Total Impurities % | 0.27 | 1.63 | 1.72 | 2.52 | 4.46 | 7.22 | 8.38 |

TABLE 3

Formulation B (with TPGS)-25/60; ON 01210 Na (50 mg/ml)

| Test | Day 0 | Day 4 | Day 7 | Day 14 | Day 28 | Day 60 | Day 90 |
|---|---|---|---|---|---|---|---|
| Appearance-Color | Clear | Clear | Clear | Clear | Clear | Clear | Clear |
| Appearance-Particles | None | None | None | None | None | None | None |
| Ph | 8.32 | 8.34 | 8.33 | 8.31 | 8.38 | 8.38 | 8.35 |
| Assay (mg/ml) | 50.9 | 49.6 | 50.0 | 50.7 | 49.7 | 49.2 | 47.3 |
| Total Impurities % | 0.07 | 0.06 | 0.14 | 0.00 | 0.11 | 0.25 | 0.17 |

The results in Table 3 for Formulation B with stabilizing agent TPGS (Example III) show that it is more stable at 25° C. and 60% humidity when compared to the results for Formulation A without stabilizing agent TPGS (Example II Table 2.)

Example V

Physical Stability Data

The formulations prepared in Examples II (without TPGS) and III (with TPGS) were compared for their physical stability at 40° C. and 75% humidity by monitoring them over a six months period. Table 4 shows physical data for Formulation A without stabilizing agent TPGS of Example II in comparison to Table 5 comprising data for Formulation B with stabilizing agent TPGS of Example III at 40° C. and 75% humidity.

TABLE 4

Formulation A (without TPGS)-40/75; ON 01210. Na (50 mg/ml)

| Test | Day 0 | Day 4 | Day 7 | Day 14 | Day 28 | Day 60 | Day 90 |
|---|---|---|---|---|---|---|---|
| Appearance-Color | Clear | Clear | Clear | Clear | Clear | Yellow | Yellow |
| Appearance-Particles | None | None | None | None | Fine | Small | Small |
| pH | 8.40 | 8.19 | 8.14 | 8.05 | 7.89 | 7.76 | 7.69 |
| Assay (mg/ml) | 50.3 | 45.9 | 45.7 | 45.1 | 42.9 | 41.5 | 40.0 |
| Total Impurities % | 0.27 | 5.24 | 5.92 | 7.33 | 11.01 | 13.45 | 14.55 |

TABLE 5

Formulation B (with TPGS)-40/75; ON 01210. Na (50 mg/ml)

| Test | Day 0 | Day 4 | Day 7 | Day 14 | Day 28 | Day 60 | Day 90 |
|---|---|---|---|---|---|---|---|
| Appearance-Color | Clear | Clear | Clear | Clear | Clear | Clear | Clear |
| Appearance-Particles | None | None | None | None | None | None | None |
| Ph | 8.32 | 8.29 | 8.32 | 8.29 | 8.30 | 8.33 | 8.30 |
| Assay (mg/ml) | 50.9 | 49.5 | 49.9 | 51.0 | 49.5 | 48.6 | 47.2 |
| Total Impurities % | 0.07 | 0.06 | 0.13 | 0.00 | 0.07 | 0.28 | 0.30 |

The results in Table 5 for Formulation B with TPGS (Example III) show that this formulation is more stable at 40° C. and 75% humidity when compared to the results for Formulation A without stabilizing agent TPGS (Example II Table 4.)

Example VI

Radioprotective Efficacy

The formulation prepared in Example III was tested for its radioprotective/radiomitigation efficacy when administered either subcutaneously or orally by gavage. Male C3H/HeN were randomly divided into 6 groups of 10 mice per group. The formulation and the corresponding placebo were administered 24 hour and 15 min prior to whole body irradiation for radioprotection studies. For the radiomitigation study the formulation was administered orally at +24 and +36 hours post irradiation. The dose of the drug was 500 mg/Kg/administration. Mice were placed in a clear pie-shaped container (N=10) with multiple holes for breathing. The container with mice was placed on a turn table inside the irradiator and irradiated at 7.5 Gy. Radiation source was 137-cesium and the mice were irradiated at a dose rate of 0.7 Gy per minute. After irradiation, mice were returned to their original cages for observation and provided free access to food and water. The survival data from this experiment are shown in FIGS. 5 and 6, respectively.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In one embodiment, the disclosure of this invention specifically removes and provisos out any prior formulations of αβ unsaturated aryl sulfone that were formulated in the absence of a water soluble Vitamin E derivative in the final formulation. The vitamin E derivatives within the scope of the invention includes, by way of example and not limitation, Vitamin E TPGS, Tocopheryl succinate, 6-Hydroxy-2,5,7,8-tetramethylchroman-2-carboxylic Acid (Trolox), and tocopherol monoglucoside (TMG), among others.

EQUIVALENTS

The invention illustratively described herein suitably may be practiced in the absence of any element or elements, limitation or limitations which is not specifically disclosed herein. Thus, for example, in each instance herein any of the terms "comprising," "consisting essentially of," and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. An aqueous pharmaceutical solution composition comprising between about 20 mg/ml to about 100 mg/ml of a radioprotective compound having the formula (I):

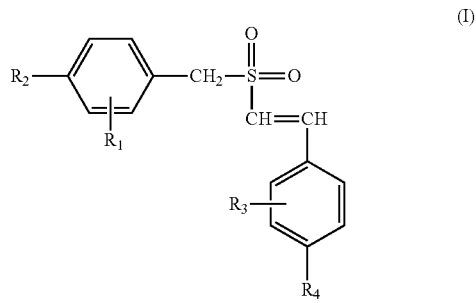

wherein $R_1$ and $R_3$ are hydrogen, $R_2$ is halogen and $R_4$ is carboxy and the steric configuration around the double bond is E, or a salt thereof, and at least one cosolvent comprising polyethylene glycol (PEG), polypropylene glycol, polyglycerol, DMA, propylene glycol, glycerol, ethanol, sorbitol, isopropyl alcohol, or a combination thereof in an amount between about 25% and about 90% w/v, and a stabilizing agent which is Vitamin E TPGS, wherein the composition has a pH within the range of about 7.0 to about 9.5.

2. The composition of claim 1, wherein the radioprotective compound is (E)-4-carboxystyryl-4-chlorobenzylsulfone.

3. The composition of claim 1, wherein the compound is the sodium salt of (E)-4-carboxystyryl-4-chlorobenzylsulfone (ON 01210.Na).

4. The composition of claim 3 which comprises between about 20 mg/ml to about 100 mg/ml of the compound (ON 01210.Na); at least one buffer selected from the group consisting of Tris-EDTA, sodium citrate, potassium citrate, sodium phosphate, potassium phosphate, sodium bicarbonate, potassium bicarbonate, lysine-HCl; Arginine-HCl; a cosolvent within the range of about 40% w/v to about 60% w/v; and Vitamin E TPGS in an amount between about 0.1% and about 10% wherein the composition has a pH within the range of about 8 to about 9.

5. The composition of claim 4 which comprises Tris-EDTA buffer composed of Tris within the range of about 0.005M to about 0.5M and EDTA within the range of about 0.0005M to about 0.05M; PEG within the range of about 40% w/v to about 60% w/v; and Vitamin E TPGS in an amount between about 0.1% and about 10% wherein the composition has a pH within the range of about 8.3 to about 8.7.

6. The composition of claim 5 which comprises Tris-EDTA buffer composed of Tris within the range of about 0.1M to about 0.3M and EDTA within the range of about 0.01M to about 0.03M; PEG 400 within the range of about 40% w/v to about 60% w/v; and Vitamin E TPGS in an amount between about 0.25% and about 5% wherein the composition has a pH within the range of about 8.3 to about 8.7.

7. The composition of claim 6 which comprises between about 20 mg/ml to about 60 mg/ml of the compound (ON 01210.Na); Tris-EDTA composed of Tris within the range of about 0.15M to about 0.25M and EDTA within the range of about 0.015M to about 0.025M; PEG 400 within the range of about 45% w/v to about 55% w/v; and Vitamin E TPGS in an amount between about 0.5% and about 2.5% wherein the composition has a pH within the range of about 8.4 to about 8.6, and the compound is substantially stable in the composition at about 25° C. for at least about 120 days.

8. The composition of claim 7 which comprises about 25 mg/ml or about 50 mg/ml of the compound (ON 01210.Na); about 0.2M Tris-EDTA buffer composed of Tris of about 0.2M and EDTA of about 0.02M; about 50% w/v PEG 400; and, about 1% Vitamin E TPGS wherein the composition has a pH within the range of about 8.4 to about 8.6, and the compound is substantially stable in the composition at about 25° C. for at least about 175 days.

9. The composition of claim 8 administered by a parenteral route.

10. The composition of claim 8 administered by a topical route.

11. The composition of claim 8 administered using an auto-injecting device.

12. The composition of claim 8 administered by oral route.

13. A pharmaceutical kit comprising one or more containers filled with the pharmaceutical compositions of the invention comprising between about 20 mg/ml to about 100 mg/ml of a radioprotective compound having the formula (I):

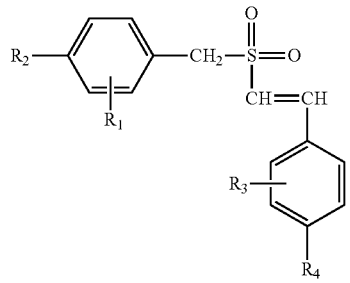

wherein $R_1$ and $R_3$ are hydrogen, $R_2$ is halogen and $R_4$ is carboxy and the steric configuration around the double bond is E, or a salt thereof, and at least one cosolvent comprising polyethylene glycol (PEG), polypropylene glycol, polyglycerol, DMA, propylene glycol, glycerol, ethanol, sorbitol, isopropyl alcohol, or a combination thereof in an amount between about 25% and about 90% w/v, and a stabilizing agent which is Vitamin E TPGS, wherein the composition has a pH within the range of about 7.0 to about 9.5, a notice in the form prescribed by a governmental agency regulating the manufacture, use or sale of the pharmaceuticals, and an instruction for use of the pharmaceutical for human administration.

14. The Kit of claim 13 wherein the radioprotective compound is ON 01210.Na.

* * * * *